(12) United States Patent
Johansson et al.

(10) Patent No.: US 8,553,837 B2
(45) Date of Patent: Oct. 8, 2013

(54) METHOD AND TOMOSYNTHESIS APPARATUS TO SHOW A PREDETERMINED VOLUME SEGMENT OF AN EXAMINATION SUBJECT

(75) Inventors: Katrin Johansson, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 63 days.

(21) Appl. No.: 13/222,285

(22) Filed: Aug. 31, 2011

(65) Prior Publication Data
US 2012/0051500 A1    Mar. 1, 2012

(30) Foreign Application Priority Data
Aug. 31, 2010 (DE) .......................... 10 2010 035 920

(51) Int. Cl.
*A61B 6/00* (2006.01)
*A61B 6/04* (2006.01)

(52) U.S. Cl.
USPC .............................................. 378/22; 378/37

(58) Field of Classification Search
USPC .......................................... 378/23, 25, 37, 22
See application file for complete search history.

(56) References Cited

U.S. PATENT DOCUMENTS

| 5,872,828 | A * | 2/1999 | Niklason et al. ................. 378/23 |
| 7,245,694 | B2 | 7/2007 | Jing et al. |
| 7,292,675 | B1 | 11/2007 | Li et al. |
| 2001/0038681 | A1 * | 11/2001 | Stanton et al. ................... 378/55 |
| 2003/0095624 | A1 * | 5/2003 | Eberhard et al. ................ 378/37 |
| 2006/0269041 | A1 * | 11/2006 | Mertelmeier .................... 378/37 |
| 2007/0036265 | A1 * | 2/2007 | Jing et al. ......................... 378/37 |
| 2007/0036272 | A1 * | 2/2007 | Johansson et al. ............ 378/108 |
| 2008/0101537 | A1 * | 5/2008 | Sendai ............................. 378/23 |
| 2009/0190819 | A1 | 7/2009 | Fischer et al. |
| 2010/0061614 | A1 * | 3/2010 | Hanke et al. .................. 382/132 |
| 2010/0135456 | A1 * | 6/2010 | Jing et al. ........................ 378/22 |

* cited by examiner

*Primary Examiner* — Alexander H Taningco
(74) *Attorney, Agent, or Firm* — Schiff Hardin LLP

(57) ABSTRACT

A method to show a predetermined volume segment of an examination subject by means of a tomosynthesis apparatus, and a correspondingly designed tomosynthesis apparatus, operate as follows. A radioscopy test is implemented in which x-rays with a defined radiation dose are generated by an x-ray source, the x-rays traversing the predetermined volume segment and strike a detector, and an intensity of the x-rays striking the detector is determined. A first radiation dose of x-rays is calculated to create a two-dimensional exposure depending on the determined radiation dose and the intensity. A second radiation doses of x-rays is calculated to implement a tomosynthesis depending on the determined radiation dose and the intensity. A tomosynthesis of the predetermined volume segment is implemented with x-rays that traverse the predetermined volume segment and strike the detector, the x-rays being generated by an x-ray source with the second radiation doses.

18 Claims, 3 Drawing Sheets

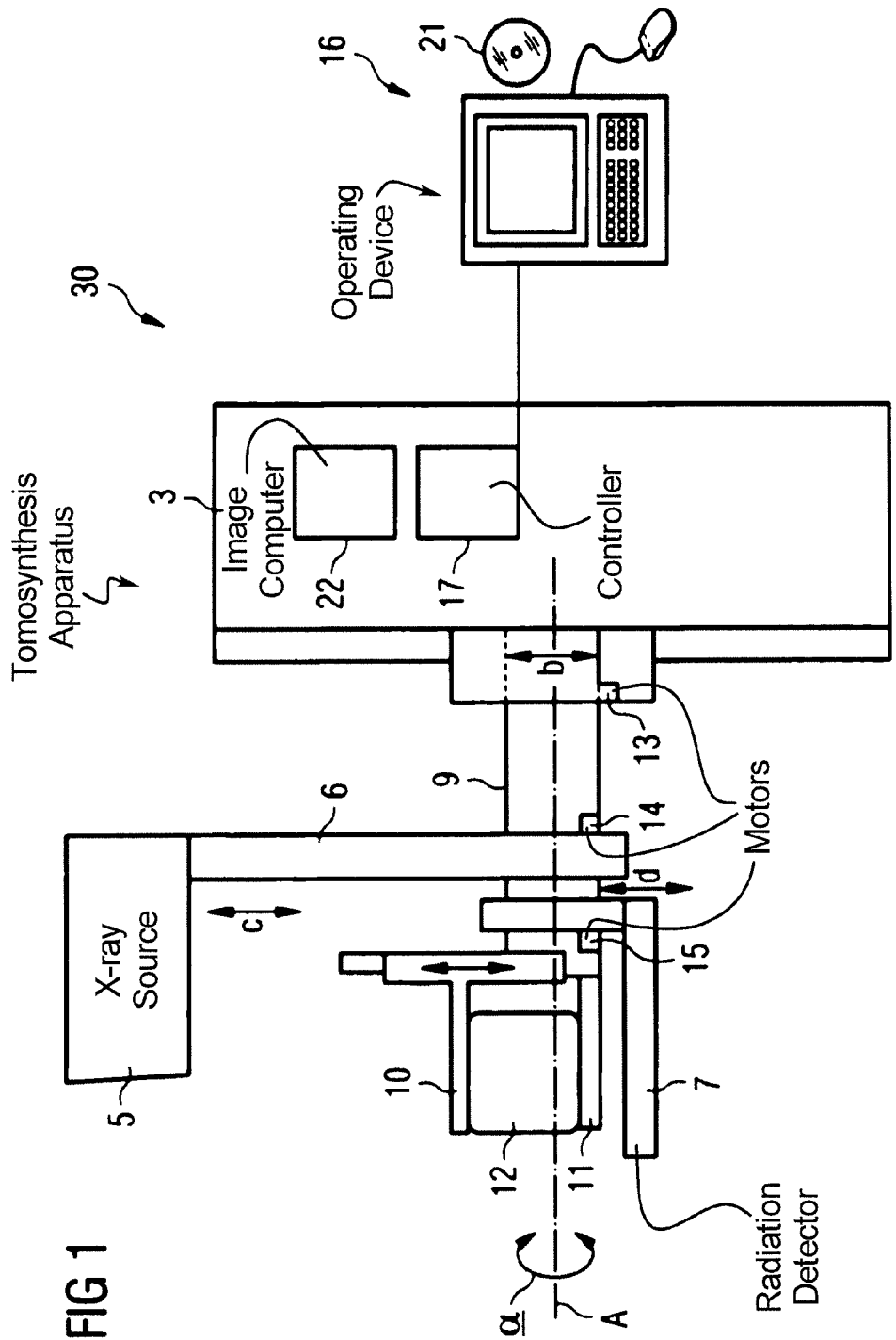

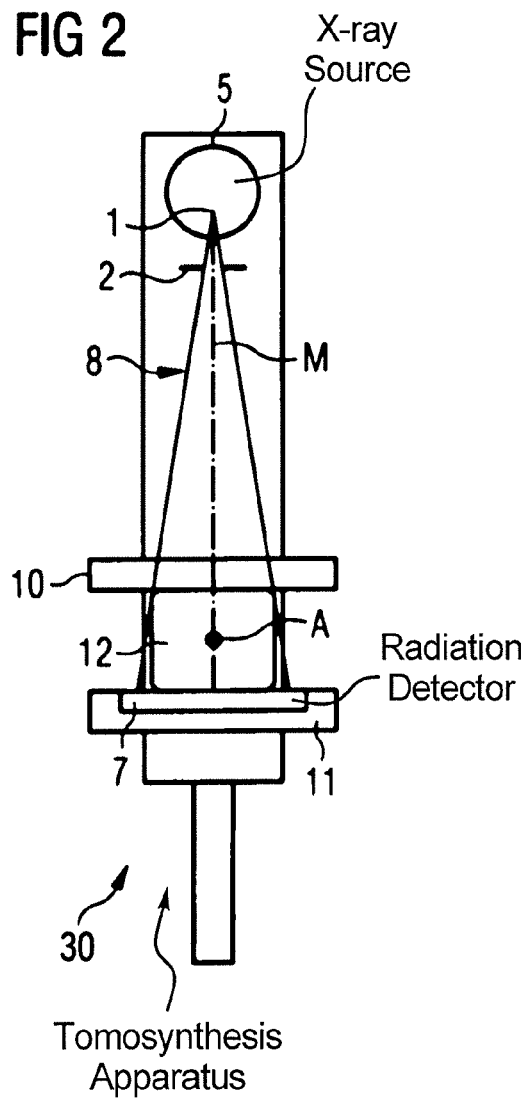
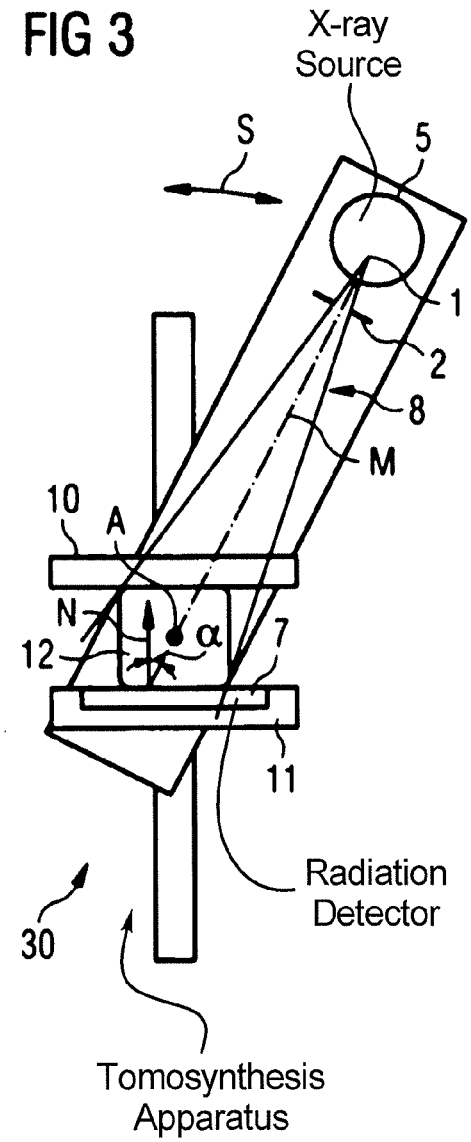

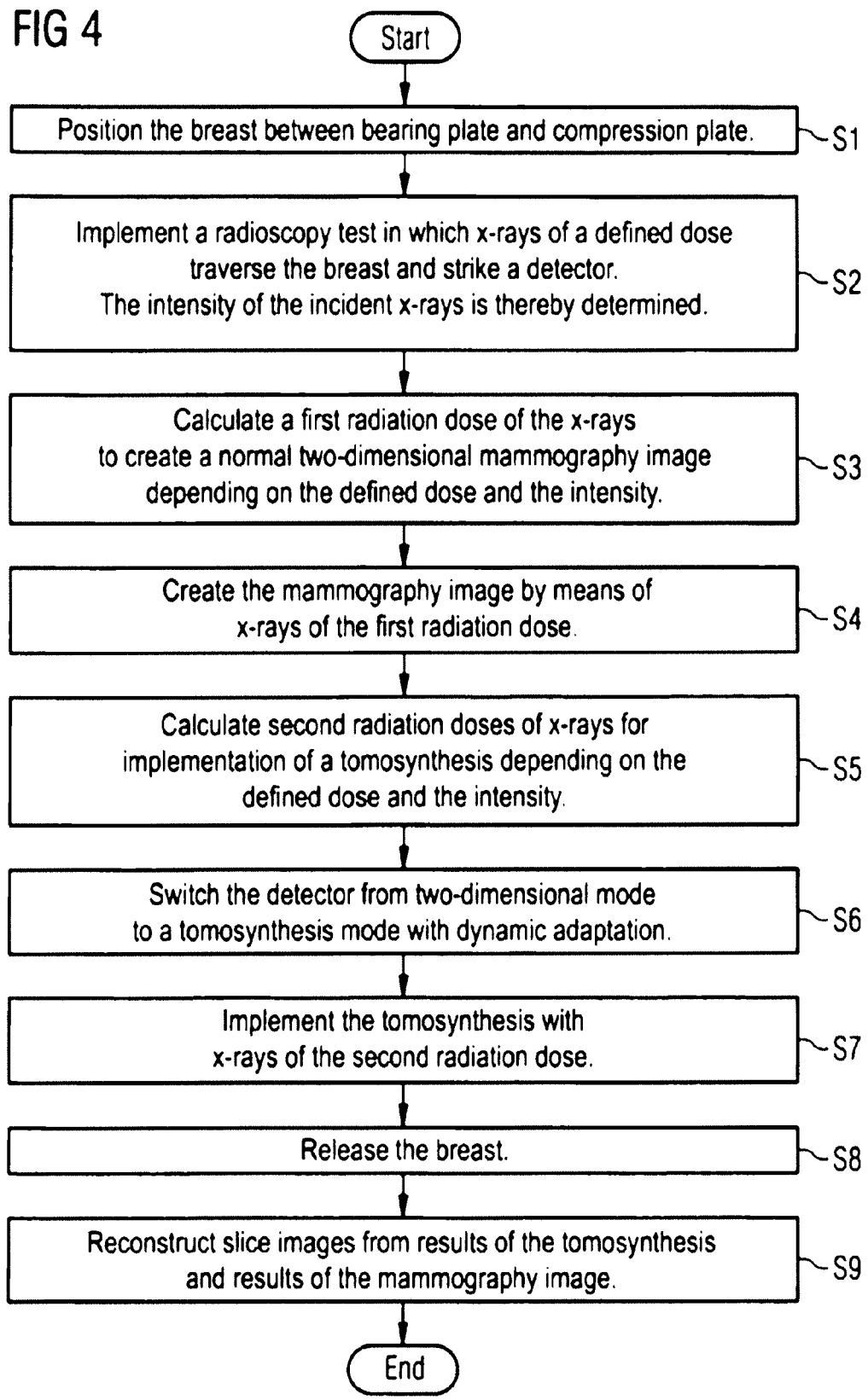

METHOD AND TOMOSYNTHESIS APPARATUS TO SHOW A PREDETERMINED VOLUME SEGMENT OF AN EXAMINATION SUBJECT

BACKGROUND OF THE INVENTION

1. Field of the Invention

The present invention concerns a method in order to generate slice images of a predetermined volume segment of an examination subject by means of tomosynthesis, as well as a correspondingly designed tomosynthesis apparatus.

2. Description of the Prior Art

U.S. Pat. No. 7,245,694 describes a method for imaging a breast, wherein both a mammography and a tomosynthesis are used.

It is currently possible to implement both a tomosynthesis and a mammogram to examine the female breast in particular for tumors. For this purpose, the breast is positioned and compressed between a bearing plate and a compression plate of the tomosynthesis apparatus. According to the prior art it is thereby typical that this procedure (which is not very comfortable for the patient) is implemented both once for the tomosynthesis and once for the mammogram (thus twice in total) since, according to the prior art, the mammogram and the tomosynthesis are two methods that are normally implemented separately.

For this reason (because these are two separate methods) it is also atypical according to the prior art to use specific results of the mammogram or, respectively, tomosynthesis to improve the implementation of the respective other method.

SUMMARY OF THE INVENTION

An object of the present invention is to design a combined implementation of a mammogram and a tomosynthesis to be more comfortable for the patient, and to combine the mammogram and the tomosynthesis such that results of the one procedure can also be used for the implementation of the respective other procedure.

Within the scope of the present invention, a method is provided to show a predetermined volume segment of an examination subject (in particular a female breast) by means of a tomosynthesis apparatus. The method according to the invention includes the following steps:

A radioscopy test or pre-shot is implemented in which an x-ray source of the tomosynthesis apparatus generates x-rays with a predetermined radiation dose. The radiation dose is normally determined from the product of the high voltage (with which the x-ray source operates), the tube current and the exposure duration (activation period). In the radioscopy test an intensity or dose or, respectively, radiation amount of the x-rays striking the detector of the tomosynthesis apparatus is determined, wherein these x-rays have traversed the predetermined volume segment of the examination subject beforehand. This intensity is dependent on the composition of the predetermined volume segment in addition to the radiation dose.

Depending on the predetermined radiation dose used in the radiation test and the determined intensity, a first radiation dose for x-rays to create a two-dimensional exposure (mammogram, for example) is calculated in order to achieve a sufficient image quality depending on the tissue of the examination subject.

Moreover, a total radiation dose or multiple second radiation doses for x-rays to implement a tomosynthesis are calculated or determined from the predetermined radiation dose and the determined intensity in order to achieve a sufficient image quality in the implementation of the tomosynthesis depending on the tissue of the examination subject.

In particular, a two-dimensional exposure is created (for example a mammogram implemented with a normal, automatic exposure control system), wherein x-rays with the first radiation dose are generated by the x-ray source. These x-rays traverse the predetermined volume segment and strike the detector, whereby data are created for a two-dimensional x-ray exposure.

Finally, a tomosynthesis of the predetermined volume segment is implemented, wherein during the tomosynthesis x-rays are generated only with the predetermined total radiation dose.

It is noted that the order of the individual steps does not need to correspond to the order described above. In particular, the tomosynthesis can take place before the creation of the two-dimensional exposure, wherein it is also conceivable that the two-dimensional acquisition takes place during the tomosynthesis. In the last case a first portion of the tomosynthesis scan would take place before the two-dimensional acquisition and a second portion of the tomosynthesis scan would take place after the two-dimensional acquisition. Moreover, the steps to calculate the first radiation dose or the total radiation dose can take place in a different order. It must only be ensured that the first radiation dose is calculated before the creation of the two-dimensional exposure and the total radiation dose or, respectively, the individual second radiation doses are calculated before the tomosynthesis.

Digital tomosynthesis is a combination of a digital image acquisition and image processing given a slight movement of the x-ray tube or x-ray source. Tomosynthesis has certain similarities to computer tomography (CT) but is considered a separate technique. While in computed tomography images are created during a complete 360° revolution of the x-ray source around the examination subject, in tomosynthesis the x-ray source pans only around a small angle of 40°, for example, wherein only a small number of exposures (typically between 7 and 60) is created. By the use of high-resolution detectors, a very high resolution can be achieved in planes perpendicular to what is known as the Z-axis (axis in the direction of the tomosynthesis angle 0°; see below), even when the resolution is lower in the direction of the z-axis. The primary field of use of tomosynthesis is imaging of the female breast as a supplement to or replacement of mammography.

In that the results of the pre-shot (radioscopy test) are used both to create the two-dimensional exposure (mammogram, for example) and for tomosynthesis, this pre-shot must be implemented only once for a combined creation of the two-dimensional exposure and the tomosynthesis, which advantageously reduces the radiation exposure of the patient on the one hand and on the other hand shortens the procedure time. When the combination of the creation of the two-dimensional exposure and the tomosynthesis is used in a combined mammogram and tomosynthesis, the female breast advantageously only needs to be positioned and compressed once between the support plate and the compression plate in order to implement both the mammogram and the tomosynthesis.

In the creation of the two-dimensional exposure the x-ray tube of the tomosynthesis apparatus is normally located at what is known as the 0° position, meaning that the tomosynthesis angle is 0° or the x-rays are generated such that their radiation direction is aligned parallel to the surface normal of the detector. The tomosynthesis angle of the two-dimensional exposure therefore corresponds to what is known as the CC ("cranial-caudal", from the head to the feet) alignment, which is also used in mammography.

According to a preferred embodiment according to the invention, an additional intensity or dose of the x-rays striking the detector is determined in the creation of the two-dimensional exposure. The first radiation dose which was used in the creation of the two-dimensional exposure and the additional intensity are then taken into account in the calculation of the total radiation dose for the tomosynthesis in order to better adapt the tomosynthesis to the composition of the examination subject. It must be taken into account that the x-ray detector is switched into a different operating mode (gain) in order to adapt to the lower dynamic range of the low-dose tomosynthesis projections.

In the event that the tomosynthesis is implemented or continued after the creation of the two-dimensional exposure, it is advantageous to produce a correction with regard to measurement results that have not yet decayed, which measurement results originate from the two-dimensional exposure.

The total radiation dose of the tomosynthesis normally essentially corresponds to the first radiation dose which is necessary only to create the two-dimensional exposure. It follows from this that the individual exposures implemented within the scope of the tomosynthesis are generated with a significantly lower (second) radiation dose in comparison to the first radiation dose. Since the output values of the sensor elements of the detector decline all the more slowly after an x-ray radiation the higher the radiation dose of said x-ray exposure, it is precisely after the creation of the two-dimensional exposure that it is important to implement the correction described above. Without this correction, what are known as residual images (which are generated by the creation of the two-dimensional exposure) would directly negatively affect the results of the tomosynthesis after the creation of the two-dimensional exposure.

If the temporal decay response of a detector is known (intensity as a function of time), a defined percentile of the intensity of the previous image can be subtracted from the current image, for example.

In the present invention a scatter radiation suppression can be implemented given the creation of the two-dimensional exposure and/or in the tomosynthesis.

The quality of the two-dimensional exposure and/or the quality of the results of the tomosynthesis can be improved by a suppression of scatter radiation.

An antiscatter grid is typically used in projection mammography (two-dimensional) in order to suppress scatter radiation. This is not possible in tomosynthesis due to the focused alignment of grid plates of the antiscatter grid on the x-ray focus. Therefore, there is the possibility to drive the grid used in two-dimensional acquisitions out of the field of view before the tomosynthesis acquisition, or as an alternative to not use any grid at all but rather to algorithmically suppress the scatter radiation (see for example U.S. Pat. No. 7,551,716).

In an embodiment according to the invention, the respective exact geometric position of the focal spot of the x-rays is determined per projection plane in the creation of the two-dimensional exposure and/or in the tomosynthesis.

Through the precise knowledge of the attitude of the focal spot relative to the predetermined volume segment and relative to the detector, the results of the tomosynthesis can in particular be improved with regard to their position information.

In principle, two different procedures are possible to determine the acquisition geometry. Either the acquisition geometry is measured as well online during the acquisition (for example with a navigation system), or the system is mechanically very stable, such that a calibration of the geometry takes place in advance, wherein the geometry is determined with a marker phantom. Alternatively, hybrids are used. The x-ray tube thereby moves stably on an orbit, wherein the angle of a projection can vary slightly, however, which is why the angle of the acquisition is measured online as well.

Moreover, according to the invention it is possible that a shielding of the tomosynthesis apparatus (face shield) is driven out automatically before the creation of the two-dimensional exposure and/or before the tomosynthesis in order to protect the body parts (in particular the face) of the patient that are not to be exposed from x-ray radiation.

Within the scope of the present invention, a tomosynthesis apparatus with a detector and an x-ray source to emit x-ray radiation is also provided. An examination subject (in particular a female breast) can be positioned between the x-ray source and the detector so that the x-rays traverse a predetermined volume segment of the examination subject before they strike the detector. The tomosynthesis apparatus comprises a controller to activate the x-ray source and the detector, and an image computer in order to receive data of the predetermined volume segment (the data being acquired by the detector) and to create multiple images from these data. The controller is in the position to control the x-ray source to implement a radioscopy test (pre-shot) such that the x-ray source generates x-rays of a predetermined radiation dose which strike the detector after they have traversed the predetermined volume segment. An intensity of the x-rays striking the detector can thereby be determined for the controller. Depending on the predetermined radiation dose and the determined intensity, the controller is in the position to calculate a first radiation dose of x-rays to create a two-dimensional x-ray image in order in particular to achieve a desired image quality with an optimally low radiation dose. Moreover, depending on the predetermined radiation dose and the determined intensity the controller is also in the position to calculate a total radiation dose or second radiation dose of x-rays to implement a tomosynthesis, in particular in order to achieve a desired quality of the results of the tomosynthesis with an optimally low total radiation dose. Finally, the tomosynthesis apparatus is able to implement a tomosynthesis of the predetermined volume segment with the calculated total radiation dose.

The advantages of the tomosynthesis apparatus according to the invention correspond to the advantages of the method according to the invention.

The present invention also encompasses a non-transitory, computer-readable storage medium encoded with programming instructions, in particular a computer program or software, that can be loaded into a memory of a programmable controller or computer of a tomosynthesis apparatus. All or various embodiments of the method according to the invention that are described above can be executed with this storage medium when the programming instructions run in the controller or control device of the tomosynthesis apparatus. The storage medium may require program means—for example libraries and auxiliary functions—in order to realize the corresponding embodiments of the method. The software can be source code (C++, for example) that must still be compiled (translated) and linked or that only must be interpreted, or an executable software code that has only to be loaded into the corresponding computer for execution.

The electronically readable data storage medium may be a DVD, a magnetic tape or a USB stick on which is stored electronically readable control information, in particular software (see above). All embodiments according to the invention of the method described in the preceding can be implemented when this control information (software) is read from the data medium and stored in a controller or computer of a tomosynthesis apparatus.

BRIEF DESCRIPTION OF THE DRAWINGS

FIG. 1 schematically illustrates a tomosynthesis apparatus according to the invention.

FIG. 2 schematically illustrates the tomosynthesis apparatus according to the invention from a different viewing angle.

FIG. 3 shows the tomosynthesis apparatus, schematically depicted during a tomosynthesis procedure.

FIG. 4 shows a preferred embodiment of the method according to the invention in the form of a flow chart.

DESCRIPTION OF THE PREFERRED EMBODIMENTS

A tomosynthesis apparatus 30 for mammography examinations is schematically depicted in FIG. 1. The tomosynthesis apparatus 30 has a support arm 9 which is borne in a bearing such that it can pan around a horizontally running axis A (see double arrow or, respectively, angle $\alpha$). The support is arranged in a stand 3 and can be displaced vertically, as indicated with the double arrow b. Arranged on the support arm 9 are an arm provided with an x-ray source 5, a flat panel detector 7 and a compression device (consisting of a compression plate 10 and a support plate 11). A female breast 12 compressed by the compression plate 10 and the support plate 11 is schematically depicted in FIG. 1. The arm 6 can be pivoted relative to the support arm 1, the detector 7 and the compression device 10, 11. Electromotors 13 through 15 of the tomosynthesis apparatus 30 are provided for height adjustments and pivot movements.

A control of the tomosynthesis apparatus 30 takes place via an operating device 16 of the tomosynthesis apparatus 30 which is connected with a controller 17 and an image computer 22 of the tomosynthesis apparatus 30. Specific methods (among these the method according to the invention) can be loaded into the controller 17 and the operating device 16 by means of a DVD 21.

FIG. 2 shows the tomosynthesis apparatus 30 given a tomosynthesis angle $\alpha$ of 0° while FIG. 3 shows the tomosynthesis apparatus 30 given a tomosynthesis angle $\alpha \neq 0°$. What is understood as a tomosynthesis angle $\alpha$ is the angle between a surface normal N of the flat panel detector 7 and the middle axis M of the x-ray beam 8. For a tomosynthesis (acquisition of a tomosynthetic image data set) the x-ray source 5 is panned in a scan direction S. As a result of the panning motion, the compressed breast 12 (which remains stationary, i.e. does not execute the panning motion) is irradiated or exposed by x-rays 8 from different angles, such that a projection presentation of the breast 12 is respectively generated from these different angles.

By a corresponding reconstruction starting from the tomosynthetic image data set (the various projection depictions), various slice images of the predetermined volume segment (the breast 12) can be generated at different depths or, respectively, levels, in particular parallel to the detector surface.

A flow chart of an embodiment of the method according to the invention is presented in FIG. 4.

After a positioning of the breast 12 between the compression plate 10 and the bearing plate 11 in Step S1, a radioscopy test or pre-shot is implemented in Step S2, in which x-rays 8 of a specific, low dose traverse the breast 12 and strike the detector 7. The intensity or the dose of the x-rays striking the detector 7 is thereby determined.

The composition of the tissue of the breast 12 to be examined can be determined depending on the determined dose and the intensity. The higher the intensity of the x-rays striking the detector 7 given the same dose of the x-rays 8 radiated towards the breast 12, the less dense the tissue and/or the smaller the compressed height of the breast 12, and the lower the dose or, respectively, total dose that must be selected for the following mammogram or tomosynthesis.

In the following Step S3 the first radiation dose for x-rays for creation of a two-dimensional mammography image is determined depending on the determined dose and the intensity. For this the first radiation dose is determined such that, depending on the tissue of the breast 12 which was examined (exposed) by means of the pre-shot, the average input dose (i.e. the average value under the breast) on the detector 7 lies in an optimal range of the sensor elements of the detector 7. For this it must be ensured that signals of the densest tissue range which delivers the lowest pixel values, up to signals at the skin or, respectively, at the edge of the breast where the highest pixel values are achieved that correspond nearly to a direct exposure, all lie in a linear range of the detector. So that this is the case, the first radiation dose is determined such that the average input dose corresponds to 3 to 6% of the maximum pixel value of the detector. For example, if the pixel values of the individual pixels of the detector 7 have a value range from 0 to $2^{12}$ or 0 to $2^{14}$, the first radiation dose should be defined such that a pixel value between 100 and 500 (depending on the detector properties) is achieved in the middle (under the breast). For example, if the low radiation dose used in the pre-shot leads to a median pixel value (for example for a sought value of 300), the first radiation dose for the mammography image could be selected to be higher by a factor of 10 than the radiation dose of the pre-shot. The radiation dose of the pre-shot is thereby normally markedly smaller than the first radiation dose to be calculated.

In Step S4 the mammography image is created with the first radiation dose calculated beforehand. The mammography image is thereby normally created at a tomosynthesis angle $\alpha$ of 0°.

Depending on the determined low radiation dose of the pre-shot and the thereby determined intensity, the second radiation doses for implementation of the individual tomosynthesis acquisitions are now calculated in Step S5. For example, it can thereby be taken into account that, given a low-noise detector 7, the total radiation dose (the sum of the second radiation doses) of the tomosynthesis approximately corresponds to the first radiation dose for the mammography image.

After a switching of the detector 7 from two-dimensional mode (mode to create a mammography image) into a tomosynthesis mode with dynamic adaptation in Step S6, the tomosynthesis is implemented with the second radiation doses (calculated in advance) in the following Step S7.

The breast 12 is subsequently released in Step S8, and in Step S9 slice images are reconstructed from the tomosynthesis image data set which was created during the tomosynthesis implemented in Step S7, wherein image data of the mammography image created in Step S4 can also be incorporated.

According to the invention, the breast 12 must only be positioned and compressed once in order to create both the mammography image and the tomosynthesis image data set. In comparison to the prior art, in which the breast must be respectively positioned and compressed once for both the mammography and for the tomosynthesis (thus twice in total), in addition to the lesser discomfort for the patient a higher patient throughput results since the time for the second positioning and compression of the breast is omitted.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to display a predetermined volume segment of an examination subject by tomosynthesis, comprising the steps of:
    operating a tomosynthesis apparatus, comprising an x-ray source and a radiation detector, to implement a radioscopy test by generating x-rays with a defined radiation dose from said x-ray source, said x-rays traversing a predetermined volume segment of a breast of an examination subject and striking said radiation detector with an intensity that is detected by said radiation detector;
    in a processor, automatically calculating a first radiation dose necessary for x-rays emitted by said x-ray source to be able to produce a two-dimensional diagnostic mammogram of the examination subject, dependent on the defined radiation dose and the detected intensity;
    in said processor, automatically calculating a second radiation dose for x-rays generated by said x-ray source to implement a tomosynthesis procedure, dependent on said defined radiation dose and the detected intensity, said second radiation dose being substantially lower than said first radiation dose; and
    operating said tomosynthesis apparatus to implement said tomosynthesis procedure by irradiating said predetermined volume segment of the breast with x-rays generated by said x-ray source from a plurality of different projection directions with x-rays being generated at each of said projection directions with said second radiation dose, said x-rays generated with said second radiation dose at each of said projection directions striking said detector after traversing the predetermined volume segment.

2. A method as claimed in claim 1 comprising generating said two dimensional diagnostic mammogram by operating said tomosynthesis apparatus to generate x-rays from said x-ray source having said first radiation dose.

3. A method as claimed in claim 2 wherein said x-rays generated by said x-ray source with said first radiation dose strike said radiation detector with an exposure intensity, and in said processor, additionally using said exposure intensity to calculate said second radiation dose.

4. A method as claimed in claim 2 comprising generating slice images of said predetermined volume segment from said two-dimensional exposure and the projections generated in said tomosynthesis procedure.

5. A method as claimed in claim 2 comprising generating said two-dimensional exposure before implementing said tomosynthesis procedure, and using measurement results that persist before implementation of said tomosynthesis procedure to correct said two-dimensional diagnostic mammogram.

6. A method as claimed in claim 2 comprising generating x-rays from said x-ray source in a direction perpendicular to said radiation detector in order to generate said two-dimensional diagnostic mammogram.

7. A method as claimed in claim 2 comprising suppressing scatter radiation during generation of said two-dimensional diagnostic mammogram.

8. A method as claimed in claim 7 comprising suppressing said scatter radiation with an antiscatter grid.

9. A method as claimed in claim 1 comprising suppressing scatter radiation during said tomosynthesis procedure.

10. A method as claimed in claim 9 comprising suppressing said scatter radiation with an antiscatter grid.

11. A method as claimed in claim 1 comprising determining a precise geometric position of a focal spot from which said x-rays are emitted from said x-ray source during generation of said two-dimensional diagnostic mammogram.

12. A method as claimed in claim 1 comprising, for each projection plane in said tomosynthesis procedure, determining a precise geometric position of a focal spot from which x-rays are emitted by said x-ray source in each projection direction.

13. A method as claimed in claim 1 comprising shielding at least one region of the examination subject, other than said predetermined volume segment, from radiation exposure during said radioscopy test.

14. A method as claimed in claim 1 comprising calculating said second radiation dose as a fraction of said first radiation dose that is approximately equal to the reciprocal of said plurality of different projection directions.

15. A tomosynthesis system comprising:
    a tomosynthesis apparatus comprising an x-ray source and a radiation detector;
    a control unit configured to operate the tomosynthesis apparatus to implement a radioscopy test by generating x-rays with a defined radiation dose from said x-ray source, said x-rays traversing a predetermined volume segment of a breast of an examination subject and striking said radiation detector with an intensity that is detected by said radiation detector;
    a processor configured to calculate a first radiation dose necessary for x-rays emitted by said x-ray source to be able to produce a two-dimensional diagnostic mammogram of the breast, dependent on the defined radiation dose and the detected intensity;
    said processor being configured to automatically calculate a second radiation dose for x-rays generated by said x-ray source to implement a tomosynthesis procedure, dependent on said defined radiation dose and the detected intensity, said second radiation dose being substantially lower than said first radiation dose; and
    said control unit being configured to operate said tomosynthesis apparatus to implement said tomosynthesis procedure by irradiating said predetermined volume segment with x-rays generated by said x-ray source from a plurality of different projection directions with x-rays being generated at each of said projection directions with said second radiation dose, said x-rays generated with said second radiation dose at each of said projection directions striking said detector after traversing the predetermined volume segment.

16. A tomosynthesis system as claimed in claim 15 wherein said processor is configured to calculate said second radiation dose as a fraction of said first radiation dose that is approximately equal to the reciprocal of said plurality of different projection directions.

17. A non-transitory computer-readable storage medium encoded with programming instructions, said storage medium being loaded into a computerized operating and processing unit of a tomosynthesis apparatus comprising an x-ray source and a radiation detector, said programming instructions causing said computerized operating and processing system to:
    operate the tomosynthesis apparatus to implement a radioscopy test by generating x-rays with a defined radiation dose from said x-ray source, said x-rays traversing a predetermined volume segment of a breast of an examination subject and striking said radiation detector with an intensity that is detected by said radiation detector;

automatically calculate a first radiation dose necessary for x-rays emitted by said x-ray source to be able to produce a two-dimensional diagnostic mammogram of the breast, dependent on the defined radiation dose and the detected intensity;

automatically calculate a second radiation dose for x-rays generated by said x-ray source to implement a tomosynthesis procedure, dependent on said defined radiation dose and the detected intensity, said second radiation dose being substantially lower than said first radiation dose; and operate said tomosynthesis apparatus to implement said tomosynthesis procedure by irradiating said predetermined volume segment with x-rays generated by said x-ray source from a plurality of different projection directions with x-rays being generated at each of said projection directions with said second radiation dose, said x-rays generated with said second radiation dose at each of said projection directions striking said detector after traversing the predetermined volume segment.

18. A non-transitory, computer-readable storage medium as claimed in claim 17 wherein said programming instructions cause said computerized operating and processing system to calculate said second radiation dose as a fraction of said first radiation dose that is approximately equal to the reciprocal of said plurality of different projection directions.

* * * * *